United States Patent
Brown et al.

(10) Patent No.: US 11,623,948 B2
(45) Date of Patent: Apr. 11, 2023

(54) PROCESS FOR PREPARATION OF SECRETORY IGA AND SECRETORY IGM

(71) Applicants: Stephen C. Brown, Ann Arbor, MI (US); Michael R. Simon, Ann Arbor, MI (US)

(72) Inventors: Stephen C. Brown, Ann Arbor, MI (US); Michael R. Simon, Ann Arbor, MI (US)

( * ) Notice: Subject to any disclaimer, the term of this patent is extended or adjusted under 35 U.S.C. 154(b) by 1014 days.

(21) Appl. No.: 16/401,322

(22) Filed: May 2, 2019

(65) Prior Publication Data

US 2019/0256577 A1 Aug. 22, 2019

Related U.S. Application Data

(60) Division of application No. 14/476,559, filed on Sep. 3, 2014, now Pat. No. 10,385,117, which is a continuation of application No. 13/935,417, filed on Jul. 3, 2013, now abandoned.

(51) Int. Cl.
| | |
|---|---|
| *B01D 15/38* | (2006.01) |
| *C07K 16/00* | (2006.01) |
| *C07K 16/06* | (2006.01) |
| *C07K 14/735* | (2006.01) |
| *C07K 16/18* | (2006.01) |
| *C07K 1/14* | (2006.01) |
| *A61K 39/00* | (2006.01) |

(52) U.S. Cl.
CPC ........ *C07K 16/00* (2013.01); *C07K 14/70535* (2013.01); *C07K 16/065* (2013.01); *C07K 16/18* (2013.01); *A61K 2039/505* (2013.01); *B01D 15/3804* (2013.01); *C07K 1/14* (2013.01); *C07K 2317/21* (2013.01); *C07K 2319/036* (2013.01); *C07K 2319/10* (2013.01); *C07K 2319/32* (2013.01)

(58) Field of Classification Search
CPC .................. C07K 16/00; C07K 14/70535; C07K 16/065; C07K 1/14; C07K 2319/10; A61K 2039/505; B01D 15/3804
See application file for complete search history.

(56) References Cited

FOREIGN PATENT DOCUMENTS

WO  WO-2013132052 A1 * 9/2013 ............. A61P 17/02

OTHER PUBLICATIONS

Jones, "Purification of polymeric immunoglobulin form cell culture supernatants by affinity chromatography using secretory component" 1987, 104(1-2), pp. 237-243 (Year: 1987).*

* cited by examiner

*Primary Examiner* — Daniel E Kolker
*Assistant Examiner* — James L Rogers
(74) *Attorney, Agent, or Firm* — MaxGoLaw PLLC

(57) ABSTRACT

A process for synthesizing and separating secretory IgA from a mixture of IgA monmer and IgA dimer is provided. The process includes covalently binding affinity tagged or epitope tagged recombinant secretory component to the IgA dimer in the mixture and binding the affinity tagged or an epitope tagged secretory IgA to immobilized moieties on the solid phase support resin to which the affinity tag or epitope tag binds and then eluting the affinity tagged or an epitope tagged secretory IgA with release buffer. A process for synthesizing and separating secretory IgM from a mixture of IgM and other plasma proteins is also provided. The process includes covalently binding affinity tagged or an epitope tagged recombinant secretory component to the IgM in the mixture and binding the affinity tagged or an epitope tagged secretory IgM to immobilized moieties on the solid phase support resin and then eluting the peptide tagged secretory IgM with a release buffer.

19 Claims, 2 Drawing Sheets

PROCESS FOR PREPARATION OF SECRETORY IGA AND SECRETORY IGM

RELATED APPLICATIONS

This application is a divisional of U.S. patent application Ser. No. 14/476,559 filed Sep. 3, 2014, now U.S. 10,385,117 B2 that in turn is a continuation of U.S. patent application Ser. No. 13/935,417 filed Jul. 3, 2013; the contents of which are hereby incorporated by reference.

FIELD OF THE INVENTION

This invention relates in general to a process for the preparation of secretory IgA and secretory IgM from plasma proteins containing IgA and/or IgM, and in particular to a process that is scalable to allow the production of commercial quantities of medicaments containing the same.

BACKGROUND OF THE INVENTION

*Clostridium difficile* (*C. difficile*) is a gram-positive anaerobic bacillus. Disease is associated with *C. difficule* infection.

Antibiotic associated pseudomembranous colitis results from the use of broad-spectrum antibiotic agents such as clindamycin. These antibiotics cause diarrhea in about 10% of treated patients and pseudomembranous colitis in about 1%. *C. difficile* causes antibiotic associated diarrhea and almost all cases of pseudomembranous colitis.

Pseudomembranous colitis results from the production of *C. difficile* toxin A (MW, 308,000) and toxin B (MW, 270,000) in the colon (Barroso et al., Nucleic Acids Res., 18:4004; Dove et al., Infect. Immun., 58:480-488; Lyerly et al., Clin. Microbiol. Rev., 1:1-18). Toxin A probably causes most of the gastrointestinal symptoms because of its enterotoxic activity (Lyerly et al., Infect. Immun., 35:1147-1150; Lyerly et al., Infect. Immun., 47:349-352). The toxins may act synergistically and the initial pathology caused by toxin A allows toxin B to manifest its toxicity (Lyerly et al., Infect. Immun., 47:349-352).

Most patients with *C. difficile* associated disease are treated effectively with vancomycin or metronidazole. Other treatment modalities include tolevemer, a toxin binding polymer (T. J. Louie et al., Clin. Infect. Dis. 2006; 43:411), and an antiparasitic medication, nitazoxanide (Med. Letter Drugs Ther. 2006; 48:89). Current treatments for *C. difficile* associated disease use antibiotics such as metronidazole and vancomycin. These drugs result in further disruption of the intestinal flora and are associated with a 20-25% incidence of disease relapse. Therefore, there is still a need for additional treatments of *Clostridium difficile* associated disease in humans.

Immunological treatment is valuable against *C. difficile*. Vaccination against toxins A and B stimulates active immunity against *C. difficile* disease in animals (Libby et al., Infect. Immun., 36:822-829).

Passive immunization is another immunological treatment against *C. dfficile*. Serum antibodies against *C. difficile* have been shown to protect hamsters against *C. difficile* disease after oral administration. Passive immunization with bovine antibodies has been proposed as a treatment for other infectious diseases of the gastrointestinal tract, such as diseases caused by rotavirus, enteropathogenic and enterotoxigenic *Escherichia coli*, *Vibrio cholerae*, and *Cryptosporidium parvum*. Preliminary studies indicate that such passive immunization provides protection (Boesman-Finkelstein et al., Infect. Immun., 57:1227-1234; Brussow et al., J. Clin. Microbiol., 25:982-986; Fayer et al., Infect. Immun., 58:2962-2965; Hilpert et al., J. Infect. Dis., 156:158-166; Mietens et al., Eur. J. Pediatr., 132:239-252; Tacket et al., N. Engl. J. Med., 318:1240-1243; Yoshiyama et al., Immunology, 61:543-547).

It has been reported that bovine immunoglobulin G (IgG) concentrate from the colostrum of cows vaccinated with *C. difficile* toxoid protects hamsters against antibiotic associated cecitis. The hamsters were protected when treated before the onset of diarrhea but not after diarrhea began (Lyerly et al., Infection and Immunity, Vol. 59, No. 6, pages 2215-2218 (1991)). IgG directed against toxins A and B of *C. difficile* are present in the general population (Bacon and Fekety, Diagn. Microbiol. Infect. Dis., 1994; 18:205-209). Human intravenous immunoglobulin derived from plasma donors has facilitated treatment in some patients, especially patients who lack circulating antibodies to the *C. difficile* toxins (Leung D. Y. et al., J. Pediatr. 1991 April; 118 (4 (Pt 1)):633-7; Salcedo J. et al., Gut 1997; 41:366-370; Wilcox M. H., J. Antimicrob. Chemoth. 2004; 53:882-884; McPherson S. et al., Dis. Colon Rectum 2006; 49:640-645; Cone L. A. et al., Infect. Dis. Clin. Pract. 2006; 14:217-220).

In vitro experiments have demonstrated that polymeric IgA is superior to monomeric IgA and IgG in preventing *C. difficile* toxin damage to intestinal epithelial cell monolayers (Stubbe H. et al., J. Immunol. 2000; 164:1952-1960). Selective neutralization of *C. difficile* toxin by serum IgA has also been demonstrated (Johnson S. et al., Infect. Immun. 1995; 63:3166-3173).

Administration of an immunoglobulin product containing specific antibodies to *C. difficile* results in the elimination of *C. difficile* toxins and also killing of the bacteria within the colon as detailed in U.S. Pat. No. 5,773,000. Such passive immunization therefore provides an effective approach for the treatment of *C. difficile* associated diseases such as colitis, pseudomembranous colitis and antibiotic associated diarrhea. This is especially important for patients experiencing multiple relapses.

Oral human immunoglobulin treatment has shown efficacy in treating acute *C. difficile* infections. Monomeric IgA admixed with IgG (2:1) was derived from plasma (IgAbulin, Immuno, Vienna) (100 mg/mL); four mL administered orally 3 times daily for 3 weeks to a three and one-half year old child with antibiotic-associated diarrhea and *C. difficile* toxin A in his stools proved effective in the context of concurrent vancomycin administration. The child improved on this treatment (Tjellstrom B. et al., Lancet 1993; 341: 701702). This report demonstrates the efficacy of passive immunization with IgA derived from the general population.

The isolation of secretory forms of immunoglobulins is more difficult that securing forms of a respective immunoglobulin that circulate in the blood and lack secretory component.

Thus, there exists a need for IgA and IgM therapeutics that are resistant to gastrointestinal tract degradation. There also exists a need to provide such a therapeutic in a dosing form well suited for treating an infected subject. Human plasma derived IgA and IgM has been successfully combined with recombinant secretory component to produce secretory IgA and secretory IgM with biological activity (Longet et al 2013).

SUMMARY OF THE INVENTION

A process for the preparation of secretory IgA and/or secretory IgM and their separation from unwanted other substances including proteins is provided. The process involves the application of an IgA source, which may contain a mixture of monomers and dimers, or a plasma protein solution containing IgM, to secretory component that is modified to contain an affinity tag or an epitope tag to form secretory IgA and/or secretory IgM containing said affinity tag or epitope tag that is useful for capture by a solid phase support resin. The protein solution which now contains the affinity tagged or epitope -tagged secretory IgA or affinity tagged or epitope-tagged secretory IgM is then applied to a solid phase support resin. The adherence of the affinity tagged or epitope tagged secretory IgA or secretory IgM to the resin and the unwanted components flow through and are thus removed. The desired product, secretory IgA or secretory IgM is then eluted from the solid phase support resin using a release agent.

For histidine and "FLAG" peptides, examples of the moieties on the solid phase support resin to which the peptide binds are immobilized divalent cations or anti polyhistidine antibodies and immobilized anti-FLAG peptide antibodies. A new composition of histidine tagged secretory IgA or secretory IgM is also provided.

DETAILED DESCRIPTION OF THE PREFERRED EMBODIMENTS

Figure 1:
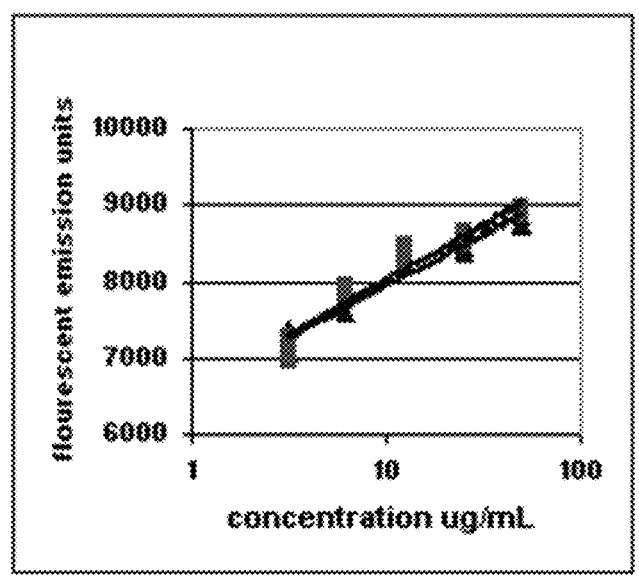
FIG. 1. ELISA Δ colostral secretory IgA (sIgA) and ☐ synthesized sIgA. Plate was coated with mouse anti-secretory component antibody.

The present invention has utility for the preparation of secretory IgA or secretory IgM. In some inventive embodiments, the IgA is derived from a mixture of monomeric and dimeric plasma IgA. or in other inventive embodiments, the preparation of secretory IgM is derived from a mixture of IgM with other plasma proteins. The present invention is superior to monomeric IgA or pentameric IgM administered orally because the presence of secretory component protects the IgA or IgM from digestion in the gastrointestinal tract. Without intending to be bound to particular theory, it is believed that the increased efficacy of the present invention is achieved for secretory IgA or secretory IgM owing to the propensity of monomeric IgA and pentameric IgM to degrade in the gastrointestinal tract. The resultant dosing requirements increase treatment costs. While the present invention is further detailed principally with respect to IgA, it is appreciated that the process and medicaments that result are equally applicable to IgM and the resulting secretory IgM, regardless of whether the tag is retained or removed.

An affinity tag or an epitope tag that are efficaceous for the present invention is one of: peptide tags:AviTag, a peptide allowing biotinylation by the enzyme BirA so the protein can be isolated by streptavidin; GLNDIFEAQKIEWHE (SEQ ID No. 1); calmodulin-tag, a peptide bound by the protein calmodulin (KRRWKKNFIAVSAANRFKKISSS-GAL (SEQ ID No. 2); FLAG-tag, a peptide recognized by an antibody DYKDDDDK (SEQ ID No. 3); Hemaglutinin-tag, a peptide recognized by an antibody YPYDVPDYA (SEQ ID No. 4); His-tag, 5-10 histidines bound by a nickel or cobalt or other divalent cation chelate HHHHHH (SEQ ID No. 6); Myc-tag, a short peptide recognized by an antibody EQKLISEEDL (SEQ ID No. 7); S-tag KET-AAAKFERQHMDS (SEQ ID No. 8); SBP-tag, a peptide which binds to streptavidin MDEKTTGWRGGHVVEG-LAGELEQLRARLEHHPQGQREP (SEQ ID No. 9); Softag 1, for mammalian expression SLAELLNAGLGGS (SEQ ID No. 10); Softag 3, for prokaryotic expression TQDPSRVG (SEQ ID No. 11); V5 tag, a peptide recognized by an antibody GKPIPNPLLGLDST (SEQ ID No. 12); Xpress tag DLYDDDDK (SEQ ID No. 13); Biotin Carboxyl Carrier Protein, a protein domain recognized by streptavidin; Glutathione-S-transferase-tag, a protein which binds to immobilized glutathione; Green fluorescent protein-tag, a protein which is spontaneously fluorescent and can be bound by nanobodies; Maltose binding protein-tag, a protein which binds to amylose agarose; Nus-tag; Strep-tag, a peptide which binds to streptavidin, or the modified streptavidin called streptactin Strep-tag II: WSHPQFEK (SEQ ID No. 14); Thioredoxin-tag; TC tag; or Ty tag.

Plasma IgA contains a mixture of monomer and dimer (Delacroix et al. 1981; Delacroix et al. 1983; Longet et al. 2013). In some embodiments of the present invention, plasma dimeric IgA in the naturally occurring monomer-dimer mixture is covalently bound to recombinant peptide tagged secretory component in vitro. In other inventive embodiments native secretory component is covalently bonded to one or more amino acid residues through conventional synthetic techniques (Hermanson GT 1996). As an example using a histidine tag, it is appreciated that a single histidine residue or a poly histidine having typically between 2 and 20 histidine residues is added to secretory component, regardless of whether produced by recombinant, synthetic addition, or other technique. The secretory IgA is now histidine tagged by virtue of the divalent bonding of the histidine tagged secretory component to the IgA dimer, The novel method of obtaining purified secretory IgA that is thus formed is to remove the secretory IgA that is now tagged by affinity binding of one of the aforementioned tags to a binding moiety immobilized on a resin a or simply by a histidine residue(s) tagged to an immobilized nickel$^{+2}$ resin. Alternatively, other immobilized divalent metal ions such as cobalt, zinc, copper or iron can be used. Alternatively, a FLAG peptide is used in certain inventive embodiments and antibody to the FLAG peptide is immobilized on the solid support resin. FLAG tags have been detailed elsewhere as for example U.S. Pat. No. 4,703,004. The resultant secretory IgA has utility, for example, as a treatment of *C. difficile* IgA associated diseases such as *Clostridium difficile* colitis, pseudomembranous colitis and antibiotic associated diarrhea and in particular to secretory immunoglobulin A (IgA) compositions administered in the form of pharmaceutical compositions. The above process is equally applicable to IgM to form purified secretory IgM.

A more detailed description of an exemplary isolation of an IgA component as a byproduct from pooled human plasma or hyperimmune pooled human plasma is as follows. Ethanol fractionation of pooled human plasma is a well-known process to prepare immunoglobulin G. Pooled human plasma is first obtained from licensed plasmapheresis centers in the United States and tested for various pathogens including the HIV virus. The first manufacturing step of most commercial immunoglobulin G preparations involves a modified cold ethanol fractionation according to Cohn to produce Cohn fraction II. In the fractionation process, many infectious viruses are eliminated from the pooled human plasma. Following fractionation, the Cohn fraction II is subjected to adsorption onto an ion exchange medium. This step may selectively reduce the IgA concentration to less than 0.1%. Such a step is important for producing immunoglobulin G for intravenous infusion into humans. This is because some individuals undergo an anaphylactic-like reaction if treated with intravenous IgG that contains IgA as an impurity.

The modified cold ethanol fractionation process according to Cohn is a series of fractionations using various levels of ethanol, pH, and temperature to produce a fraction II which is further treated to produce immunoglobulins as described above. In the fractionation process, pooled human plasma is first treated to produce a cryoprecipitate and cryo-supernatant. Alternatively, it is appreciated that the source plasma may be autologous plasma or hyperimmune human plasma, either pooled, or from a single individual who has been immunized against a specific disease.

In another embodiment, the IgA component is be prepared by hybridoma techniques to provide antigen-specific IgA. Hybridoma techniques are described originally in Kohler and Milstein, Nature 1975; 256:495-497 with more recent advances summarized in Berzofsky et al., Fundamental Immunology, Third Edition, 1993, pp 455-62.

Regardless of the source, the cryo-supernatant is subjected to a first ethanol fractionation to yield a supernatant I. Supernatant I is subjected to a second ethanol fractionation to yield fraction II+III. Fraction II+III is subjected to a third ethanol fractionation procedure to yield a supernatant III and Fraction III precipitate.

The fraction III precipitate enriched in IgA is generally discarded as an unwanted byproduct. According to the present invention, this unwanted IgA following ion exchange adsorption purification is further treated by incubation with immobilized hydrolases to inactivate viruses and vasoactive substances. Such treatment has been proven to eliminate many viruses tested including HIV, Sindbis, and vaccinia. Other antiviral treatments, as known to those skilled in the art, are used in combination and consist of solvent detergent processes, nanofiltration and/or heat inactivation. Usually three antiviral steps are implemented. Following incubation to remove viruses, the concentration of the active material is adjusted with sterile saline or buffered solutions to ensure a constant amount of active material per milliliter of reconstituted product. Finally, the solution with a constant amount of reconstituted product is sterilized by filtration before use.

The ethanol fractionation process according to Cohn is well known in the art and is described in Cohn et al., J. Am. Chem. Soc. 1946; 68:459-475, Oncley et al., J. Am. Chem. Soc. 1949; 71:541-550, and in most detail in pages 576-602, Kirk-Othmer Encyclopedia of Chemical Technology, Vol. 3, second edition (1963). Alternatively, ion exchange chromatography may be used to obtain the dimeric and polymeric IgA byproduct during the manufacture of intravenous immunoglobulin. From 4% to 22% of plasma IgA is dimeric and polymeric IgA (Delacroix et al. 1981; Delacroix et al. 1983). The resulting dimeric IgA-J chains are purified to form a medicament.

The dimeric and polymeric IgA present in the plasma IgA monomer-polymer mixture is further coupled to secretory component that is recombinantly produced to include a histidine tag or another of the aforementioned tags; or subsequently covalently bonded to a peptide tag such as histidine or poly-histine oligopeptide. In certain inventive embodiments, the coupling of IgA to secretory component is accomplished by forming disulfide bonds under mildly oxidizing conditions. (Jones R. M. L., Schweikart F., Frutiger S., Jaton J-C., Hughes G. J. Thiol-disulfide redox buffers maintain a structure of immunoglobulin A that is essential for optimal in vitro binding to secretory component. Biochimica et Biophysica Acta 1998; 1429:265-274.) Dimeric and polymeric IgA containing both J chain and secretory component is purified from the mixture by immobilized metal ion affinity chromatography, as performed by those of skill in the art of protein purification.

It has been previously found that it is possible to separate recombinant proteins from cell supernates by producing such proteins with histidine tails or other of the aforementioned tags and then passing the cell supernates through nickel bound solid support resins. The histidine or other tag adheres to the nickel or other suitable tag specific binding moiety and is retained while the unwanted proteins are washed through. The tagged secretory immunoglobulin protein is then recoverd by eluting it with an imidazole buffer in the case of an amide-metal bond between target protein and resin (Block H et al 2009).

The mixture of histidine tagged secretory IgA and residual monomeric IgA is buffer exchanged into a binding buffer containing low concentrations of imidazole (≤40 mM). Another release agent operative to exchange histidine tagged secretory IgA or secretory IgM illustratively includes 1) ethylene diamine tetraacetic acid (EDTA) at 10 mM and 2) an elution buffer of pH 5.5 or lower. Typical binding buffer imidazole concentrations range from 0.1 to 100 millimolar (mM). It is appreciated that the initial binding buffer pH is somewhat variable and readily discerned for a given chemical structure of buffer and concentration through routine experimentation. The chromatography medium operative herein is selected to be stable in the presence of the binding buffer and able to separate histidine tagged secretory IgA. Suitable media illustratively include Exemplary of these media are nickel, cobalt and zinc immobilized on sepharose. In a preferred embodiment, the affinity medium is washed in a wash buffer containing from 0 to 100 mM imidazole to remove unbound monomeric IgA. The bound histidine tagged secretory IgA is recovered using an elution buffer of a higher imidazole concentration (e.g. 100 to 1000 mM). With successive elutions separation of monomeric from histidine tagged secretory component bound dimeric IgA is exacted. It is appreciated that the inventive process is amenable to scaling to produce quantities sufficient to treat numerous subjects. It is appreciated that similar selective binding pairs is achieved between other inventive tagged secretory component containing immunoglobulin proteins and resins are conventional to the art for each of the aforementioned tags.

By way of a specific example, the binding and wash buffers are 50 mM $NaH_2PO_4$ 300 mM NaCl and 20 mM imidazole, is adjusted to pH 8. The mixture of IgA monomer and secretory IgA is dissolved in that buffer. The elution buffer is identical to the binding buffer with the exception that the imidazole is at a higher concentration, e.g 100 to 1000 mM.

Figure 2:
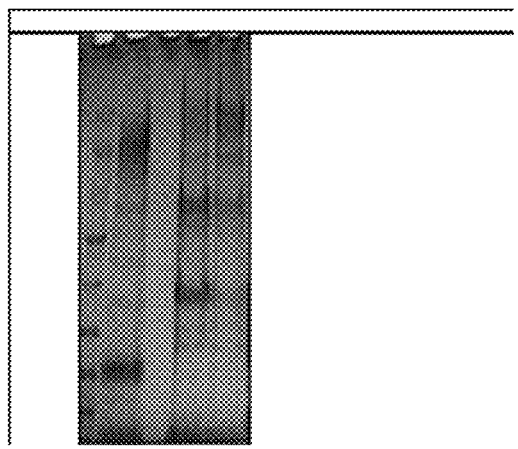
FIG. 2. Tris acetate PAGE showing sIgA, prepared with histidine tagged secretory component eluted from nickel resin (Cube Biotech, Monheim, Germany). Lane 1: MW ladder; Lane 2: colostral secretory IgA; Lane 3 blank; Lane 4 nickel resin flow-through; Lane 5: nickel resin imidazole eluate with semisynthetic sIgA.

The remaining histidine tagged secretory IgA is then eluted from the divalent immobilized metal resin with the elution buffer according to conventional techniques and conditions that include an exemplary basic pH of for example 8 to 10, see FIGS. 1 and 2.

Purified secretory IgA containing histidine tagged secretory component is stabilized in some embodiments for example by the addition of human serum albumin to a final concentration of 5% total weight albumen.

In another embodiment, the tag is removed from the recovered secretory IgA and native secretory IgA is available for usage as a medicament. For a histidine tagged secretory IgA a procedure for tag removal is known to the art (Kopera E et al 2012).

In summary, the inventive process is the addition of tagged secretory component in either recombinant or post expression tagging to a mixture of plasma derived IgA monomers and dimers, in which the tagged secretory component combines with the IgA dimer forming secretory IgA and allows recovery of the newly formed secretory IgA by adhesion to immobilized divalent metal ions or other solid phase moiety, and subsequent elution therefrom.

Plasma IgM can be recovered from the byproducts of the production of intravenous immunoglobulin. An example of such a byproduct is Cohn fraction III precipitate. The IgM is most easily solubilized from Cohn fraction III precipitate by 20 mM sodium acetate. Other plasma proteins are similarly solubilized along with the IgM. The plasma IgM in this protein mixture is covalently bound to recombinant histidine tagged secretory component in vitro forming secretory IgM within the protein mixture. The secretory IgM is now tagged by virtue of the divalent bonding of the tagged secretory component to the IgM. The novel method of obtaining purified secretory IgM that is thus formed is to remove the secretory IgM that is now tagged by affinity binding of the tag to a immobilized nickel$^{+2}$ or other divalent metal ion or other suitable binding moiety conventional to the art that is part of a resin column. The resultant semisynthetic secretory IgM has utility, for example, as a treatment of *Clostridium difficile* associated diseases such as *Clostridium difficile* colitis, pseudomembranous colitis and antibiotic associated diarrhea and in particular to secretory immunoglobulin M compositions administered in the form of pharmaceutical compositions.

In another embodiment, the tag is removed from the recovered secretory IgM and native secretory IgM is available for usage as a medicament. For a histidine tagged secretory IgM a procedure for tag removal is known to the art (Kopera E et al 2012).

Thus, an inventive process provides the addition of peptide tagged secretory component to a mixture of plasma derived IgM and other plasma proteins, in which the peptide tagged secretory component combines with the IgM forming secretory IgM and allows recovery of the newly formed secretory IgM by adhesion to moieties on the solid phase support resin to which the peptide binds, and subsequent elution therefrom using an elution buffer.

REFERENCES

Aoyama K, Chiba J. Separation of different molecular forms of mouse IgA and IgM monoclonal antibodies by high-performance liquid chromatography on spherical hydroxyapatite beads. J Immunol Methods. 1993; 162 (2): 201-10.

Bacon A. E. 3rd, Fekety R. Immunoglobulin G directed against toxins A and B of *Clostridium difficile* in the general population and patients with antibiotic-associated diarrhea. Diagn. Microbiol. Infect. Dis. 1994; 18:205-209.

Barroso L. A., Wang S. Z., Phelps C. J., Johnson J. L., Wilkins T. D. Nucleotide sequence of *Clostridium difficile* toxin B gene. Nucleic Acids Res. 1990; 18:4004.

Berzofsky J. A., Berkower I. J., Epstein S. L., Monoclonal Antibodies in Chapter 12, Antigen-Antibody Interactions and Monoclonal Antibodies, pp. 455-465 in Fundamental Immunology, Third Edition, W. E. Paul (ed), Raven Press, NY 1993. Berzofsky et al., Fundamental Immunology, Third Edition, 1993, pp 455-462.

Block H, Maertens B, Spriestersbach A, Brinker N, Kubicek J, Fabis R, Labahn J, Schafer F. Immobilized-Metal Affinity Chromatography (IMAC): A Review. CHAPTER 27 in Methods in Enzymology, Volume 463, 2009.

Boesman-Finkelstein M., Walton N. E., Finkelstein R. A. Bovine lactogenic immunity against cholera toxin-related enterotoxins and Vibrio cholerae outer membranes. Infect. Immun. 1989; 57:1227-1234.

Brussow H., Hilpert H., Walther I., Sidoti J., Mietens C., Bachmann P. Bovine milk immunoglobulins for passive immunity to infantile rotavirus gastroenteritis. J. Clin. Microbiol. 1987; 25:982-986.

Cohn E. J., Strong L. E., Hughes W. L., Jr., Mulford D. J., Ashworth J. N., Melin M., Taylor H. L., Preparation and Properties of Serum and Plasma Proteins IV. A System for the Separation into Fractions of the Protein and Lipoprotein Components of Biological Tissues and Fluids, J. Am. Chem. Soc. 1946; 68; 459-475.

Cone L. A., Lopez C., Tarleton H. L., Jodoin D., Taylor M., Gade-Andavolu R., Dreisbach L. P. A durable response to relapsing *Clostridium difficile* colitis may require combined therapy with high-dose oral vancomycin and intravenous immune globulin. Infect. Dis. Clin. Pract. 2006; 14:217-220.

Corthesy B., Recombinant Secretory IgA for Immune Intervention Against Mucosal Pathogens, Biochem. Soc. Trans. 1997, 25; 471-475.

Corthier et al., Emergence in Gnotobiotic Mice of Non-toxinogenic Clones of *clostridium difficile* from a Toxinogenic One, Infection and Immunity, June 1988, pp. 1500-1504.

Corthier et al., Protection Against Experimental Pseudomembranous Colitis in Gnotobiotic Mice by Use of Monoclonal Antibodies Against *clostridium difficile* Toxin A, Infection and Immunity, March 1991, pp. 1192-1195.

Crottet P., Cottet S., Corthesy B., Expression, Purification and Biochemical Characterization of Recombinant Murine Secretory Component, A Novel Tool in Mucosal Immunology, Biochem. J. 1999, 341; 299-306.

Delacroix D. L., Hodgson H. J., McPherson A., Dive C., Vaerman J. P. Selective transport of polymeric immunoglobulin A in bile. Quantitative relationships of monomeric and polymeric immunoglobulin A, immunoglobulin M, and other proteins in serum, bile, and saliva. J. Clin. Invest. 1982 August; 70 (2):230-41

Delacroix D. L., Elkom K. B., Geubel A. P., Hodgson H. F., Dive C., Vaerman J. P. Changes in size, subclass, and metabolic properties of serum immunoglobulin A in liver diseases and in other diseases with high serum immunoglobulin A. J. Clin. Invest. 1983 February; 71 (2):358-67.

Dove C. H., Wang S. Z., Price S. B., Phelps C. J., Lyerly D. M., Wilkins T. D. and Johnson J. L.; Lyerly et al. Molecular characterization of the *Clostridium difficile* toxin A gene. Infect. Immun. 1990; 58:480-488.

Ehrich et al., Production of *Clostridium difficile* Antitoxin, Infection and Immunity, June 1980, pp. 1041-1043.

Fayer R., Guidry A., Blagburn B. L. Immunotherapeutic efficacy of bovine colostral immunoglobulins from a hyperimmunized cow against cryptosporidiosis in neonatal mice. Infect. Immun., 1990; 58:2962-2965.

Gerding et al., *Clostridium difficile*-Associated Diarrhea, Archives of Internal Medicine, vol. 146, January 1986, pp. 95-100.

Hermanson G T. Bioconjugate Techniques. Academic Press, San Diego 1996.

Hilpert H., Brussow H., Mietens C., Sidoti J., Lerner L., Werchau H. Use of bovine milk concentrate containing antibody to rotavirus to treat rotavirus gastroenteritis in infants. J. Infect. Dis. 1987; 156:158-166.

Johnson S. et al. Infect. Immun. 1995; 63:3166-3173.

Jones R. M. L., Schweikart F., Frutiger S., Jaton J-C., Hughes G. J. Thiol-disulfide redox buffers maintain a structure of immunoglobulin A that is essential for optimal in vitro binding to secretory component. Biochimica et Biophysica Acta 1998; 1429:265-274.

Kelly et al., *Clostridium difficile* Colitis, New England Journal of Medicine, vol. 330, January 1994, pp. 257-262.

Kelly et al., Human Colonic Aspirates Containing Immunoglobulin A Antibody to *Clostridium difficile* Toxin A Inhibit Toxin A-Receptor Binding, Gastroenterology, vol. 102, No. 1, pp. 35-40.

Kohler G., Milstein C., Continuous Cultures of Fused Cells Secreting Antibody of Predetermined Specificity, Nature 1975; 256; 495-497.

Kopera E, Belczyk-Ciesielska A, Bal W. Application of Ni(II)-assisted peptide bond hydrolysis to non-enzymatic affinity tag removal. PLoS One. 2012; 7 (5):e36350. doi: 10.1371/journal.pone.0036350. Epub 2012 May 4.

Leung D. Y., Kelly C. P., Boguniewicz M., Pothoulakis C., LaMont J. T., Flores A. Treatment with intravenously administered gamma globulin of chronic relapsing colitis induced by *Clostridium difficile* toxin. J. Pediatr. 1991 April; 118 (4 (Pt 1)):633-637.

Libby J. M., Jortner B. S., Wilkins T. D. Effects of the two toxins of *Clostridium difficile* in antibiotic-associated cecitis in hamsters. Infect. Immun. 1982 May; 36 (2):822-829.

Lima et al., Effects of *Clostridium difficile* Toxins A and B in Rabbit Small and Large Intestine In Vivo and on Cultured Cells In Vitro, Infection and Immunity, March 1988, pp. 582-588.

Longet S, Miled S, Lotscher M, Miescher S M, Zuercher A W, Corthesy B. Human plasma-derived polymeric IgA and IgM antibodies associate with secretory component to yield biologically active secretory-like antibodies. J Biol Chem. 2013 Feb. 8; 288:4085-94.

Louie T. J., Peppe J., Watt C. K., Johnson D., Mohammed R., Dow G., Weiss K., Simon S., John J. F. Jr., Garber G., Chasan-Taber S., Davidson D. M.; Tolevamer Study Investigator Group. Tolevamer, a novel nonantibiotic polymer, compared with vancomycin in the treatment of mild to moderately severe *Clostridium difficile*-associated diarrhea. Clin. Infect. Dis. 2006; 43:411-20.

Luellau, E., von Stockar, U., Vogt, S., Freitag, R. Development of a downstream process for the isolation and separation of monoclonal immunoglobulin A monomers, dimers and polymers from cell culture supernatant, Journal of Chromatography A, 1998, 796:165-175.

Lullau E., Heyse S., Vogel H., Marison I., von Stockar U., Kraehanbuhl J-P., Corthesy B., Antigen Binding Properties of Purified Immunoglulin A Antibodies, J. Biol. Chem. 1996; 271:16300-16309.

Lyerly D. M., Krivan H. C., Wilkins T. D. *Clostridium difficile*: its disease and toxins. Clin. Microbiol. Rev. 1988; 1:1-18.

Lyerly D. M., Phelps C. J., Toth J., Wilkins T. D. Characterization of toxins A and B of *Clostridium difficile* with monoclonal antibodies. Infect. Immun. 1986; 54:70-76.

Lyerly D. M., Bostwick E. F., Binion S. B., Wilkins T. D. Passive immunization of hamsters against disease caused by *Clostridium difficile* by use of bovine immunoglobulin G concentrate. Infect. Immun. 1991; 59:2215-2218.

Lyerly D. M., Lockwood D. E., Richardson S. H., Wilkins T. D. Biological activities of toxins A and B of *Clostridium difficile*. Infect. Immun. 1982; 35:1147-1150.

Lyerly D. M., Saum K. E., MacDonald D. K., Wilkins T. D. Effects of *Clostridium difficile* toxins given intragastrically to animals. Infect. Immun. 1985; 47:349-352.

Mahe et al., Effect of Various Diets on Toxin Production by Two Strains of clostridium difficile in Gnotobiotic Mice, Infection and Immunity, August 1987, pp. 1801-1805.

Martinez et al., Purification and Characterization of *Clostridium sordellii* Hemorrhagic Toxin and Cross-Reactivity with *Clostridium difficile* Toxin A (Enterotoxin), Infection and Immunity, May 1988, pp. 12-15-1221.

McFarland et al., Nosocomial Acquisition of *Clostridium difficile* Infection, The New England Journal of Medicine, January 1989, pp. 204-210.

McFarland et al., Review of *Clostridium difficile* Associated Diseases, American Journal of Infection Control, vol. 14, No. 3, June 1986, pp. 99-104.

McPherson S., Rees C. J., Ellis R., Soo S. and Panter S. J. Intravenous Immunoglobulin for the Treatment of Severe, Refractory, and Recurrent *Clostridium difficile* Diarrhea. Diseases of the Colon & Rectum. 2006; 49 (5):640-645.

Med. Letter Drugs Ther. 2006; 48:89-90,92.

Mietens C., Keinhorst H., Hilpert H., Gerber H., Amster H., Pahud J. J. Treatment of infantile *E. coli* gastroenteritis with specific bovine anti-*E. coli* milk immunoglobulins. Eur. J. Pediatr. 1979; 132:239-252.

Mitchell et al., Effect of Toxin A and B of *Clostridium difficile* on Rabbit Ileum and Colon, Gut, 1986, vol. 27, pp. 78-85.

Morris et al., Role of Surgery in Antibiotic-Induced Pseudomembranous Enterocolitis, The American Journal of Surgery, vol. 160, November 1990, pp. 535-539.

Oncley J. L., Melin M., Richert D. A., Cameron J. W., Gross P. M., Jr., The Separation of the Antibodies, Isoagglutinins, Prothrombin, Plasminogen and β1-Lipoprotein into Subfractions of Human Plasma. J. Am. Chem. Soc. 1949; 71:541-550.

Pothoulakis C., LaMont J. T., Eglow R., Gao N., Rubins J. B., Theoharides T. C., Dickey B. F. Characterization of rabbit ileal receptors for *Clostridium difficile* toxin A. Evidence for a receptor-coupled G protein. J. Clin. Invest. 1991; 88:119-25.

Rothman et al., Differential Cytotoxic Effects of Toxins A and B Isolated from *Clostridium difficile*, Infection and Immunity, November 1984, pp. 324-331.

Salcedo J. et. al. Gut 1997; 41:366-370.

Strong L. E., Blood Fractionation, pp. 576-602 in vol. 3, Kirk-Othmer Encyclopedia of Chemical Technology. Second Edition, H. F. Mark, J. J. McKetta, D. F. Othmer (eds), Interscience Publishers, NY 1963, pp. 576-602.

Stubbe H. et al. J. Immunol. 2000; 164:1952-1960.

Symersky J., Novak J., McPherson D. T., DeLucas L., Mestecky J. Expression of the recombinant human immunoglobulin J chain in *Escherichia coli*. Mol. Immunol. 2000; 37:133-140.

Tacket C. O., Losonsky G., Link H., Hoang Y., Guesry P., Hilpert H., Levine M. M. Protection by milk immunoglobulin concentrate against oral challenge with enterotoxigenic *Escherichia coli*. N. Engl. J. Med. 1988; 318:1240-3.

Tjellstrom B., Stenhammar L., Eriksson S., Magnusson K. E. Oral immunoglobulin A supplement in treatment of *Clostridium difficile* enteritis. Lancet 1993; 341 (8846):701-702.

Triadafilopoulos et al., Differential Effects of *Clostridium difficile* Toxins A and B on Rabbit Ileum, Gastroenterology, 1987, vol. 93, pp. 273-279.

Tucker et al., Toxin A of *Clostridium difficile* Is a Potent Cytotoxin, Journal of Clinical Microbiology, May 1990, pp. 869-871.

Weltzin R., Traina-Dorge V., Soike K., Zhang J. Y., Mack P., Soman G., Drabik G., Monath T. P., Intranasal Monoclonal IgA Antibody against Respiratory Syncytial Virus Protects Rhesus Monkeys against Upper and Lower Respiratory Tract Infection. J. Infect. Dis. 1996; 174:256-261.

Weltzin R., Hsu S. A., Mittler E. S., Georgakopoulas K., Monath T. P., Intranasal Monoclonal Immunoglobulin A against Respiratory Synctial Virus Protects against Upper and Lower Respiratory Tract Infections in Mice. Antimicrob. Agents Chemother. 1994; 38:2785-2791.

Wilcox M. H. J. Antimicrob. Chemoth. 2004; 53:882-884.

Yoshiyama Y., Brown W. R. Specific antibodies to cholera toxin in rabbit milk are protective against Vibrio cholerae-induced intestinal secretion. Immunology. 1987; 61:543-547.

Patent applications and publications mentioned in the specification are indicative of the levels of those skilled in the art to which the invention pertains. These applications and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A process for synthesizing a secretory IgA therapeutic by separating a dimeric IgA including J chain and mixed with other proteins in a protein mixture comprising:
    adding secretory component in solution that is tagged with an affinity or epitope tag selected from the group consisting of polyhistidine, AviTag, calmodulin-tag, FLAG-tag, hemaglutinin-tag, Myc-tag, S-tag, SBP-tag, Softag 1, Softag 3, V5 tag, Xpress tag, biotin carboxyl carrier protein, glutathione-S-transferase-tag, green fluorescent protein-tag, maltose binding protein-tag, Nus-tag; Strep-tag, thioredoxin-tag; TC tag, and Ty tag; to the protein mixture, the protein mixture containing the dimeric IgA including the J chain, facilitating the covalent binding of the affinity or epitope tagged secretory component to the dimeric IgA to produce the secretory IgA therapeutic;
    exposing the protein mixture to a binding moiety immobilized on a solid phase resin under conditions that the secretory IgA therapeutic binds to the solid phase resin by interaction between the affinity or epitope tagged secretory component and the binding moiety;
    washing unbound protein mixture from the solid phase support; and
    then eluting the secretory IgA therapeutic with a release buffer from the solid phase support by the release buffer interfering with the interaction between the affinity or epitope tagged secretory component and the binding moiety.

2. The process of claim 1 wherein the secretory component is human.

3. The process of claim 1 wherein the affinity or epitope tag is removed from secretory IgA after the eluting step.

4. The process of claim 1 wherein the moiety on the solid phase support resin to which the affinity or epitope tag binds is a divalent cation.

5. The process of claim 1 wherein the secretory component is recombinant.

6. The process of claim 1 wherein the affinity or epitope tag is a polyhistidine.

7. A process for synthesizing a secretory IgA therapeutic by separating dimeric IgA including J chain and mixed with other proteins comprising:
    adding secretory component in solution that is tagged with an affinity or epitope tag selected from the group consisting of polyhistidine, AviTag, calmodulin-tag, FLAG-tag, hemaglutinin-tag, Myc-tag, S-tag, SBP-tag, Softag 1, Softag 3, V5 tag, Xpress tag, biotin carboxyl carrier protein, glutathione-S-transferase-tag, green fluorescent protein-tag, maltose binding protein-tag, Nus-tag; Strep-tag, thioredoxin-tag; TC tag, and Ty tag; to the protein mixture, the protein mixture obtained from human plasma containing the dimeric IgA including the J chain, facilitating the covalent binding of the affinity or epitope tagged secretory component to the dimeric IgA containing the J chain to produce the secretory IgA therapeutic;
    exposing the protein mixture to a binding moiety immobilized on a solid phase resin under conditions that the secretory IgA therapeutic binds to the solid phase resin by interaction between the affinity or epitope tagged secretory component and the binding moiety;
    washing unbound protein mixture from the solid phase support; and
    then eluting the secretory IgA therapeutic with a release buffer from the solid phase support by the release buffer interfering with the interaction between the affinity or epitope tagged secretory component and a binding moiety.

8. An improved process for synthesizing a secretory IgA therapeutic from a protein mixture of plasma proteins containing plasma derived IgA containing J chain, by adding secretory component that is tagged with an affinity or epitope tag to the protein mixture forming the secretory IgA therapeutic in the protein mixture wherein the improvement comprises:
    recovering the secretory IgA therapeutic from the protein mixture by adhesion to moieties on a solid phase support resin to which the affinity or epitope tag binds, and subsequent eluting the secretory IgA therapeutic using an elution buffer.

9. The improved process of claim 8 wherein the secretory component is human.

10. The improved process of claim 8 wherein the protein mixture is obtained from human plasma.

11. The improved process of claim 8 wherein the affinity or epitope tag is removed from the secretory IgA therapeutic prior to administration to a patient.

12. The improved process of claim 8 further comprising washing unbound plasma proteins including unbound immunoglobulins lacking the J chain through the resin prior to the eluting the secretory IgA therapeutic.

13. The improved process of claim 8 wherein the secretory component is recombinant.

14. The improved process of claim 8 wherein the affinity or epitope is histidine or polyhistidine and is coupled to the secretory component in vitro.

15. The improved process of claim 8 wherein the plasma derived IgA containing J chain is a combination of dimeric and polymeric IgA.

16. The process of claim 1 further comprising stabilizing the secretory IgA therapeutic by adding human serum albumin.

17. A process for synthesizing a secretory IgA and secretory IgM mixture therapeutic by separating a dimeric IgA including J chain and a pentameric IgM including J chain, both the dimeric IgA and the pentameric IgM mixed with other proteins in a protein mixture comprising:
- adding secretory component in solution that is tagged with an affinity or epitope tag selected from the group consisting of polyhistidine, AviTag, calmodulin-tag, FLAG-tag, hemaglutinin-tag, Myc-tag, S-tag, SBP-tag, Softag 1, Softag 3, V5 tag, Xpress tag, biotin carboxyl carrier protein, glutathione-S-transferase-tag, green fluorescent protein-tag, maltose binding protein-tag, Nus-tag; Strep-tag, thioredoxin-tag; TC tag, and Ty tag; to the protein mixture, the protein mixture containing the dimeric IgA including the J chain and the pentameric IgM including the J chain, facilitating the covalent binding of the affinity or epitope tagged secretory component to the dimeric IgA and to the pentameric IgM to produce the secretory IgA and secretory IgM mixture therapeutic;
- exposing the protein mixture to a binding moiety immobilized on a solid phase resin under conditions that the secretory IgA and seretory IgM mixture therapeutic binds to the solid phase resin by interaction between the affinity or epitope tagged secretory component and the binding moiety;
- washing unbound protein mixture from the solid phase support; and
- then eluting the secretory IgA and secretory IgM mixture therapeutic with a release buffer from the solid phase support by the release buffer interfering with the interaction between the affinity or epitope tagged secretory component and the binding moiety.

18. A process for synthesizing a secretory IgA and secretory IgM mixture therapeutic by separating dimeric IgA including J chain and a pentameric IgM including J chain, both the dimeric IgA and the pentameric IgM mixed with other proteins comprising:
- adding secretory component in solution that is tagged with an affinity or epitope tag selected from the group consisting of polyhistidine, AviTag, calmodulin-tag, FLAG-tag, hemaglutinin-tag, Myc-tag, S-tag, SBP-tag, Softag 1, Softag 3, V5 tag, Xpress tag, biotin carboxyl carrier protein, glutathione-S-transferase-tag, green fluorescent protein-tag, maltose binding protein-tag, Nus-tag; Strep-tag, thioredoxin-tag; TC tag, and Ty tag; to the protein mixture, the protein mixture obtained from human plasma containing the dimeric IgA including the J chain and the pentameric IgM including the J chain, facilitating the covalent binding of the affinity or epitope tagged secretory component to the dimeric IgA containing the J chain and to the pentameric IgM containing the J chain to produce the secretory IgA and secretory IgM mixture therapeutic;
- exposing the protein mixture to a binding moiety immobilized on a solid phase resin under conditions that the secretory IgA and secretory IgM mixture therapeutic binds to the solid phase resin by interaction between the affinity or epitope tagged secretory component and the binding moiety;
- washing unbound protein mixture from the solid phase support; and
- then eluting the secretory IgA and secretory IgM mixture therapeutic with a release buffer from the solid phase support by the release buffer interfering with the interaction between the affinity or epitope tagged secretory component and a binding moiety.

19. An improved process for synthesizing a secretory IgA and secretory IgM mixture therapeutic from a protein mixture of plasma proteins containing plasma derived IgA containing J chain and plasma derived IgM containing J chain, by adding secretory component that is tagged with an affinity or epitope tag to the protein mixture forming the secretory IgA and secretory IgM mixture therapeutic in the protein mixture wherein the improvement comprises:
recovering the secretory IgA and secretory IgM mixture therapeutic from the protein mixture by adhesion to moieties on a solid phase support resin to which the affinity or epitope tag binds, and subsequent eluting the secretory IgA and secretory IgM mixture therapeutic using an elution buffer.

* * * * *